(12) United States Patent
Richardson et al.

(10) Patent No.: US 7,759,321 B2
(45) Date of Patent: Jul. 20, 2010

(54) COMPOUNDS FOR THE TREATMENT OF PAIN

(75) Inventors: Peter Richardson, Cambridge (GB); Kevin Lee, Warwickshire (GB); Lisa Lione, Cambridge (GB)

(73) Assignee: Cambridge Biotechnology Ltd (GB)

( * ) Notice: Subject to any disclaimer, the term of this patent is extended or adjusted under 35 U.S.C. 154(b) by 0 days.

(21) Appl. No.: 10/547,455

(22) PCT Filed: Mar. 5, 2004

(86) PCT No.: PCT/GB2004/000935

§ 371 (c)(1),
(2), (4) Date: Jul. 26, 2006

(87) PCT Pub. No.: WO2004/078183

PCT Pub. Date: Sep. 16, 2004

(65) Prior Publication Data

US 2007/0066559 A1 Mar. 22, 2007

(30) Foreign Application Priority Data

Mar. 7, 2003 (GB) .................... 0305149.7

(51) Int. Cl.
*A61K 31/70* (2006.01)
*C07H 19/167* (2006.01)
(52) U.S. Cl. .................... 514/46; 536/27.63
(58) Field of Classification Search ............ 514/46; 536/27.63
See application file for complete search history.

(56) References Cited

U.S. PATENT DOCUMENTS

| | | | |
|---|---|---|---|
| 3,936,439 A | 2/1976 | Marumoto et al. | |
| 4,225,591 A | 9/1980 | Marumoto et al. | |
| 4,255,565 A | 3/1981 | Marumoto et al. | |
| 4,705,758 A | 11/1987 | Bruns | |
| 5,677,290 A * | 10/1997 | Fukunaga | 514/46 |
| 5,679,650 A * | 10/1997 | Fukunaga et al. | 514/46 |
| 5,683,989 A * | 11/1997 | Lau et al. | 514/46 |
| 5,877,180 A | 3/1999 | Linden et al. | |
| 5,942,497 A * | 8/1999 | Fukunaga et al. | 514/46 |

FOREIGN PATENT DOCUMENTS

| | | |
|---|---|---|
| AU | 49412/72 | 5/1974 |
| DE | 2258378 | 6/1973 |
| FR | 2162128 | 7/1973 |
| WO | WO 9638728 | 12/1996 |
| WO | WO 9934804 | 7/1999 |
| WO | WO 2004079329 | 9/2004 |

OTHER PUBLICATIONS

Ueeda et al., "Cardiovascular Actions of Adenosines, But Not Adenosine Receptors, Differ in Rat and Guinea Pig," Life Sciences, 49(18), 1351-1358 (1991).*

Makujina et al., "Structure-Activity Relationship of 2-(ar)alkoxyadenosines at the Adenosine Receptor in Coronary Artery," European Journal of Pharmacology, 243(1), 35-38 (1993).*

Herrick-Davis et al., "Evaluation of Adenosine Agonists as Potential Analgesics," European Journal of Pharmacology, 162(2), 365-369 (Mar. 21, 1989).*

Karlsten et al., "The Antinociceptive Effect of Intrathecally Administered Adenosine Analogs in Mice Correlates with the Affinity for the A1-Adenosine Receptor," Neuroscience Letters, 121(1-2), 267-270 (Jan. 2, 1991).*

Venes et al.(eds.), Taber's Cyclopedic Medical Dictionary, 19th Edition, F. A. Davis Co., Philadelphia, PA, 2001, see pp. 1092-1094 (definition of "inflammation" at col. 1 of p. 1092).*

Venes et al.(II)(eds.), Taber's Cyclopedic Medical Dictionary, 20th Edition, F. A. Davis Co., Philadelphia, PA, 2005, see pp. 665-667 (definition of "edema" beginning at col. 1 of p. 665); copy supplied by applicant.*

"Aldrich Handbook of Fine Chemicals and Laboratory Equipment," 1015-1016, (2000); XP002366927.

Askalan, R et al., "Role of Histidine Residues in the Adenosine A2A Receptor Ligand Binding Site," *Journal of Neurochemistry*, 63(4):1477-84, (1994); XP001196996.

Bartlett, R. et al., "Synthesis and Pharmacological Evaluation of a Series of Analogues of 1-Methylisoguanosine," *Journal of Medicinal Chemistry*, 24:947-54, (1981); XP002225573.

Belardinelli, L. & Isenberg, G., "Isolated Atrial Myocytes: Adenosine and Acetylcholine Increase Potassium Conductance," *The American Journal of Physiology*, 224:H734-H737, (1983).

(Continued)

*Primary Examiner*—Lawrence E Crane
(74) *Attorney, Agent, or Firm*—Fish & Richardson P.C.

(57) ABSTRACT

Compounds of the class of adenosines, represented by structural formula I, wherein R is $C_{1-4}$ alkoxy, and X is H or OH, excluding 2-methoxyadenosine, are useful as analgesics, particularly in a method of preventing, treating, or ameliorating pain which comprises administering a compound of formula I to a subject in need of such prevention, treatment, or amelioration.

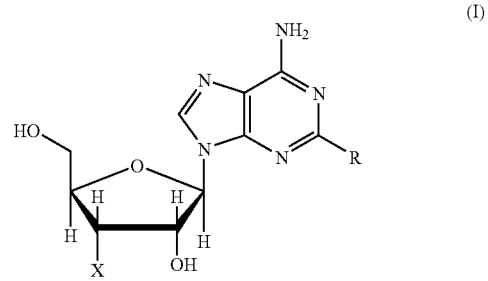

(I)

16 Claims, 6 Drawing Sheets

OTHER PUBLICATIONS

Belfrage, M. et al., "The Safety and Efficacy of Intrathecal Adenosine in Patients with Chronic Neuropathic Pain," *Anesthesia and Analgesia*, 89(1):136-42, (1999); XP009027670.

Bhakuni, D., "Biological Activity of Marine Nucleosides and their Analogues," *Proceedings of the Indian National Science Academy*. Part B Biological Sciences, 65(Part 2):97-112, (1995); XP001165752.

Bressi, J. et. al., "Adenosine Analogues as Inhibitors of Trypanosoma Brucei Phosphoglycerate Kinase: Elucidation of a Novel Binding Mode for a 2-Amino-N6-Substituted Adenosine," *Journal of Medicinal Chemistry*, 43(22):4135-50, (2000); XP000999137.

Collins, S. et al., "The Effect of GR190178, a Selective Low-Efficacy Adenosine A1 Receptor Agonist, on the Treatment of Neuropathic Hyperalgesia in the Rat," *British Journal of Pharmacology*, 133(Proceedings Supplement):48p (2001), Proceedings of the British Pharmacological Society Meeting, (Dec. 18-21, 2000); XP009027671.

Daly, J. et al., "Structure-Activity Relationships for N6-Substituted Adenosines at a Brain A1-Adenosine Receptor with a Comparison to an A2-Adenosine Receptor Regulating Coronary Blood Flow," *Biochemical Pharmacology*, 35(15):2467-81 (1986) XP009010090.

Dan, K., "Nerve Block Therapy and Postherpetic Neuralgia," *Critical Reviews in Physical and Rehabilitation Medicine*, 7(2):93-112 (1995) Embase Database Accession No. EMB-1995373280. XP002273335.

De Zwart, M. et al., "5'-N-Substituted Carboxamidoadenosines as Agonists for Adenosine Receptors," *Journal of Medicinal Chemistry*, 42(8): 1384-92 (1999) XP001002032.

Deghati, P. et al., "Regioselective Nitration of Purine Nucleosides: Synthesis of 2-Nitroadenosine and 2-Nitroinosine," *Tetrahedron Letters*, 41(8):1291-5 (2000) XP004188609.

Feoktistov, I. et al., "Adenosine A2B Receptors: A Novel Therapeutic Target in Asthma?," *Trends in Pharmacological Sciences*, 19(4):148-53 (1998) XP002287445.

Fishman, P. et al., "A3 Adenosine Receptor as a Target for Cancer Therapy," *Anti-Cancer Drugs*, 13(5):437-43 (2002) XP009024520.

Hiley, C. et al., "Effects of pH on Responses to Adenosine, CGS 21680, Carbachol and Nitroprusside in the Isolated Perfused Superior Mesenteric Arterial Bed of the Rat," *British Journal of Pharmacology*, 116(6):2641-6 (1995) XP008032448.

Jiang, Q. et al., "Mutagenesis Reveals Structure-Activity Parallels Between Human A2A Adenosine Recveptors and Biogenic Amine G Protein-Coupled Receptors," *Journal of Medicinal Chemistry*, 40(16):2588-95 (1997) XP002287314.

Kaul, P. et al., "Adenosine Agonist of Marine Origin Indicative of Two Types of Adenosinergic Receptors," *Pharmacologist*, 23(3):540 (1981) XP009027638.

Keeling, S. et al., "The Discovery and Synthesis of Highly Potent, A2a Receptor Agonists," *Bioorganic and Medicinal Chemistry Letters*, 10(4):403-6 (2000) XP004189943.

Kirk, I. et al., "Further Characterization of [3H]-CGS 21680 Binding Sites in the Rat Striatum and Cortex," *British Journal of Pharmacology*, 114(2):537-43 (1995) XP008032472.

Klitgaard, H. et al., "Contrasting Effects of Adenosine $A_1$ and $A_2$ Receptor Ligands in Different Chemoconclusive Rodent Models," *European Journal of Pharmacology*, 242:221-8 (1993).

Knabb, R. et al., "Consistent Parallel Relationships Among Myocardial Oxygen Consumption, Coronary Blood Flow, and Pericardial Infusate Adenosine Concentration with Various Interventions and Beta-Blockade in the Dog," *Circulation Research*, 53:33-41 (1983).

König, G., "Meeresorganismen als Quelle Pharmazeutisch Bedeutsamer Naturstoffe," *Deutsche Apotheker Zeitung*, 132(14):673-83 (1992) XP002255617.

Marumoto, R. et al. "Synthesis and Coronary Vasodilating Activity of 2-Substituted Adenosines," *Chemical and Pharmaceutical Bulletin*, 23(4):759-74 (1975) XP002154408.

Matova, M. et al. "QSAR Analysis of 2-Alkyloxy and 2-Aralkyloxy Adenosine A1-and A2-Agonists," *European Journal of Medicinal Chemistry*, 32(6):505-13 (1997) XP004088461.

Matsuda et al., Nucleosides and Nucleotides. XXVII. Synthesis of 2-and 8-Cyanoadenosines and their Derivatives, *Chemical and Pharmaceutical Bulletin*, 27(1):183-92 (1979) XP002127436.

Matsuda, A. et al., "Nucleosides and Nucleotides. 103. 2-Alkyladenosines: a Novel Class of Selective Adenosine A2 Receptor Agonists with Potent Antihypertensive Effects," *Journal of Medicinal Chemistry*, 35:241-52 (1992) XP002170995.

Miles, R. et al., "Nucleic Acid Related Compounds," *Journal of the American Chemical Society*, 117:5951-7 (1995) XP002366161.

Nair, V. et al., "Novel, Stable Cogeners of the Antiretroviral Compound 2', 3'-Dideoxyadenosine," *Journal of the American Chemical Society*, 111(22):8502-4 (1989) XP001105896.

Ojha, L. et al., "A Simple Method for Synthesis of Spongosine, Azaspongosine, and their Antiplatelet Effects," *Nucleosides and Nucleotiodes*, 14(9-10):1889-1900 (1995) XP009027643.

Okusa, M., "A2A Adenosine Receptor: A Novel Therapeutic Target in Renal Disease," *American Journal of Physiology*, 282(1 Part 2):F10-F18 (2002) XP002287448.

Rieger, J.M. et al., "Design, Synthesis, and Evaluation of Novel A2A Adenosine Receptor Agonists," *Journal of Medicinal Chemistry*, 44:531-9 (2001) XP002222174.

Ribeiro, J. et al., "Adenosine Receptors in the Nervous System: Pathophysiological Implications," *Progress in Neurobiology*, 68(6):377-92 (2002) XP002287447.

Sawynok, J. "Adenosine Receptor Activation and Nociception," *European Journal of Pharmacology*, 317(1):1-11 (1998) XP002273334.

Schaeffer, H. et al., "Synthesis of Potential Anticancer Agents. XIV. Ribosides of 2, 6-Disubstituted Purines," *Journal of the American Chemical Society*, 80:3738-42 (1958) XP002300926.

Smith, J. et al., "The Effects of Reduced pH on A2B Adenosine Receptor-Evoked Cyclic AMP Generation in the Guinea-Pig Cerebral Cortex," *British Journal of Pharmacology*, 123 (Proc. Suppl.): 195p (1998). Meeting of the British Pharmacological Society Held Jointly with the Dutch Pharmacological Society (Dec. 10-12, 1997) XP008032489.

Sullivan, G. et al., "Role of A2A Adenosine Receptors in Inflammation," *Drug Development Research*, 45(3/4):103-12 (1998) XP000978332.

Ueeda, M. et al., "2-Alkoxyadenosines: Potent and Selective Agonists at the Coronary Artery A2 Adenosine Receptor," *Journal of Medicinal Chemistry*, 34:1334-1339 (1991) XP002225574.

Ueeda, M. et al., "2-Aralkoxyadenosines: Potent and Selective Agonists at the Coronary Artery A2 Adenosine Receptor," *Journal of Medicinal Chemistry*, 34(4):1340-1344 (1991) XP004088461.

Umino, T. et al., "Nucleosides and Nucleotides. 200. Reinvestigation of 5'-N-Ethylcarboxamidoadenosine Derivatives: Structure-Activity Relationships for P(3) Purinoceptor-Like Proteins," *Journal of Medicinal Chemistry*, 44:208-14 (2001) XP002366162.

Vittori, S. et al., "2-Alkenyl and 2-Alkyl Derivatives of Adenosine and Adenosine-5'-N-Ethyluronamide: Different Affinity and Selectivity of E-and Z-Diastereomers at A2A Adenosine Receptors," *Journal of Medicinal Chemistry*, 39:4211-7 (1996) XP002366163.

International Search Report for PCT/GB2004/000935, dated May 26, 2004.

Ali Akbar Nekooeian et al., "Effects of adenosine $a_{2a}$ receptor agonist, cgs 21680, on blood pressure, cardiac index and arterial conductance in anaesthetized rats", 1996, European Journal of Pharmacology, vol. 307, pp. 163-169.

R.A.A. Mathôt et al., "Pharmacokinetic-haemodynamic relationships of 2-chloroadenosine at adenosine $A_1$ and $A_{2a}$ receptors in vivo", 1996, British Journal of Pharmacology, vol. 118, No. 2, pp. 369-377.

John R. Keddie et al., "In vivo characterisation of ZM 241385, a selective adenosine $A_{2a}$ receptor antagonist", 1996, European Journal of Pharmacology, vol. 301, pp. 107-113.

Randy L. Webb et al., "Development of Tolerance to the Antihypertensive Effects of Highly Selective Adenosine $A_{2a}$ Agonists upon Chronic Administration", 1993, The Journal of Pharmacology and Experimental Therapeutics, vol. 267, pp. 287-295.

R.L. Webb et al., "Cardiovascular Effects of Adenosine $A_2$ Agonists in the Conscious Spontaneously Hypertensive Rat: A Comparative Study of Three Structurally Distinct Ligands", 1991, The Journal of Pharmacology and Experimental Therapeutics, vol. 259, pp. 1203-1212.

C. Casati et al., "Telemetry Monitoring of Hemodynamic Effects Induced Over Time by Adenosine Agonists in Spontaneously Hypertensive Rats", 1995, The Journal of Pharmacology and Experimental Therapeutics, Vo. 275, pp. 914-919.

Erminio Bonizzoni et al., "Modeling Hemodynamic Profiles by Telemetry in the Rat, A Study With $A_1$ and $A_{2a}$ Adenosine Agonists", 1995, Hypertension, vol. 25, No. 4, Part 1, pp. 564-569.

Cristina Alberti et al., "Mechanism and Pressor Relevance of the Short-Term Cardiovascular and Renin Excitatory Actions of the Selective $A_{2a}$-Adenosine Receptor Agonists", 1997, Journal of Cardiovascular Pharmacology, vol. 30, No. 1, pp. 320-324.

* cited by examiner

A)

*$p<0.05$, **$p<0.01$ versus vehicle (Sidak's)

B)

A)

B)

A)

B)

C)

COMPOUNDS FOR THE TREATMENT OF PAIN

CROSS REFERENCE TO RELATED APPLICATIONS

This application is a national phase filing under 35 U.S.C. §371 of international application number PCT/GB2004/000935, filed Mar. 5, 2004, which claims the benefit of priority of British application number 0305149.7, filed Mar. 7, 2003. The disclosures of the prior applications are considered part of (and are incorporated by reference in) the disclosure of this application.

TECHNICAL FIELD

This invention relates to analgesic compounds and to methods of preventing, treating, or ameliorating pain using these compounds.

BACKGROUND

Pain has two components, each involving activation of sensory neurons. The first component is the early or immediate phase when a sensory neuron is stimulated, for instance as the result of heat or pressure on the skin. The second component is the consequence of an increased sensitivity of the sensory mechanisms innervating tissue which has been previously damaged. This second component is referred to as hyperlagesia, and is involved in all forms of chronic pain arising from tissue damage, but not in the early or immediate phase of pain perception.

Thus, hyperalgesia is a condition of heightened pain perception caused by tissue damage. This condition is a natural response of the nervous system apparently designed to encourage protection of the damaged tissue by an injured individual, to give time for tissue repair to occur. There are two known underlying causes of this condition, an increase in sensory neuron activity, and a change in neuronal processing of nociceptive information which occurs in the spinal cord. Hyperalgesia can be debilitating in conditions of chronic inflammation (e.g. rheumatoid arthritis), and when sensory nerve damage has occurred (i.e. neuropathic pain).

Two major classes of analgesics are known: (i) non steroidal anti-inflammatory drugs (NSAIDs) and the related COX-2 inhibitors; and (ii) opiates based on morphine. Analgesics of both classes are effective in controlling normal, immediate or nociceptive pain. However, they are less effective against some types of hyperalgesic pain, such as neuropathic pain. Many medical practitioners are reluctant to prescribe opiates at the high doses required to affect neuropathic pain because of the side effects caused by administration of these compounds, and the possibility that patients may become addicted to them. NSAIDs are much less potent than opiates, so even higher doses of these compounds are required. However, this is undesirable because these compounds cause irritation of the gastrointestinal tract.

Adenosine A1 receptor agonists are known to act as powerful analgesics (Sawynok, Eur J Pharmacol. (1998) 347, 1-11), and adenosine A2A receptor agonists are known to act as anti-inflammatory agents. However, development of adenosine-based therapies has generally been precluded because they have unacceptable side effects. Selective A1 receptor agonists cause bradycardia, and A2A receptor agonists cause widespread vasodilation with consequent hypotension and tachycardia.

Spongosine is a compound that was first isolated from the tropical marine sponge, *Cryptotethia crypta* in 1945 (Bergmann and Feeney, J. Org. Chem. (1951) 16, 981, Ibid (1956) 21, 226). Spongosine was the first methoxypurine found in nature, and is also known as 2-methoxyadenosine, or 9H-purin-6-amine, 9-α-D-arabinofuranosyl-2-methoxy.

The first biological activities of spongosine were described by Bartlett et al. (J. Med. Chem. (1981) 24, 947-954) who showed that this compound has muscle relaxant, hypothermic, hypotensive, and anti-inflammatory activity in rats.

The affinity of spongosine for the rat adenosine A1 and A2A receptors has been determined. The Kd values obtained (in the rat) were 340 nM for the A1 receptor and 1.4 µM for the AMA receptor, while the EC50 value for stimulation of the rat A2A receptor was shown to be 3 µM (Daly et al., Pharmacol. (1993) 46, 91-100). In the guinea pig, the efficacy of spongosine was tested in the isolated heart preparation and the EC50 values obtained were 10 µM and 0.7 µM for the adenosine A1 and A2A receptors, respectively (Ueeda et al J Med Chem (1991) 34, 1334-1339).

In the early 1990s the other adenosine receptors (the A2B and A3 receptors) were cloned, but the activity of spongosine at these receptors was never investigated. The low potency and poor receptor selectivity of this compound led to it being largely ignored as more and more potent and receptor selective novel compounds were synthesised.

SUMMARY AND DETAILED DESCRIPTION

There is, therefore, a need to provide analgesics which are sufficiently potent to control pain perception in neuropathic, inflammatory, and other hyperalgesic syndromes, and which do not have serious side effects or cause patients to become addicted to them.

It has surprisingly been found that spongosine when administered to mammals can give significant pain relief in conditions of increased pain sensitivity (such as neuropathic and inflammatory hyperalgesia), without causing the significant side effects expected from use of purine receptor agonists. The activity of spongosine as an analgesic is the subject of International patent application no. PCT/GB03/05379 (unpublished at the filing date of the present application).

It is believed that other compounds of formula (I) also have analgesic activity and can be administered with reduced probability and severity of side effects compared to other adenosine receptor agonists:

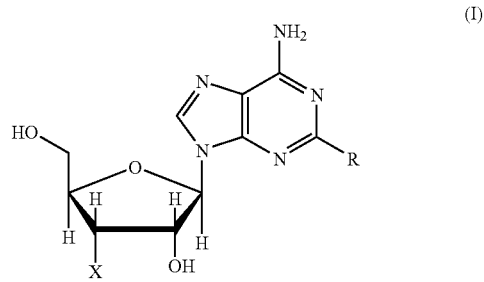

wherein R is $C_{1-4}$ alkoxy, and X is H or OH. Preferably R is $C_{1-4}$ alkoxy, and X is OH.

According to the invention there is provided use of a compound of formula (I) in the manufacture of a medicament for the prevention, treatment, or amelioration of pain, particularly hyperalgesia.

There is also provided according to the invention a method of preventing, treating, or ameliorating pain (particularly hyperalgesia) which comprises administering a compound of formula (I) to a subject in need of such prevention, treatment, or amelioration.

Preferred compounds of formula (I) are 2-methoxyadenosine (although this compound may be excluded in view of PCT/GB03/05379), 2-ethoxyadenosine, and 2-butyloxyadenosine.

Compounds of formula (I) are believed to be effective in inhibiting pain perception in mammals suffering from pain, in particular neuropathic and inflammatory pain, even when administered at doses expected to give plasma concentrations well below those known to activate adenosine receptors. In addition, after administration of spongosine, no effect on normal physiological nociception was observed. Therefore, compounds of formula (I) can treat pain (particularly neuropathic and inflammatory pain) without causing the significant side effects associated with administration of other adenosine receptor agonists, and also without reducing normal sensory perception.

As mentioned above hyperalgesia is a consequence in most instances of tissue damage, either damage directly to a sensory nerve, or damage of the tissue innervated by a given sensory nerve. Consequently, there are many conditions in which pain perception includes a component of hyperalgesia.

According to the invention there is provided use of a compound of formula (I) as an analgesic (particularly an anti-hyperalgesic) for the prevention, treatment, or amelioration of pain (particularly hyperalgesia) caused as a result of neuropathy, including Diabetic Neuropathy, Polyneuropathy, Cancer Pain, Fibromyalgia, Myofascial Pain Syndrome, Osteoarthritis, Pancreatic Pain, Pelvic/Perineal pain, Post Herpetic Neuralgia, Rheumatoid Arthritis, Sciatica/Lumbar Radiculopathy, Spinal Stenosis, Temporo-mandibular Joint Disorder, HIV pain, Trigeminal Neuralgia, Chronic Neuropathic Pain, Lower Back Pain, Failed Back Surgery pain, back pain, post-operative pain, post physical trauma pain (including gunshot, road traffic accident, burns), Cardiac pain, Chest pain, Pelvic pain/PID, Joint pain (tendonitis, bursitis, acute arthritis), Neck Pain, Bowel Pain, Phantom Limb Pain, Obstetric Pain (labour/C-Section), Renal Colic, Acute Herpes Zoster Pain, Acute Pancreatitis Breakthrough Pain (Cancer), Dysmenorhoea/Endometriosis.

According to the invention there is also provided use of a compound of formula (I) as an analgesic (particularly an anti-hyperalgesic) for the prevention, treatment, or amelioration of pain (particularly hyperalgesia) caused as a result of inflammatory disease, or as a result of combined inflammatory, autoimmune and neuropathic tissue damage, including rheumatoid arthritis, osteoarthritis, rheumatoid spondylitis, gouty arthritis, and other arthritic conditions, cancer, HIV, chronic pulmonary inflammatory disease, silicosis, pulmonary sarcosis, bone resorption diseases, reperfusion injury (including damage caused to organs as a consequence of reperfusion following ischaemic episodes e.g. myocardial infarcts, strokes), autoimmune damage (including multiple sclerosis, Guillam Barre Syndrome, myasthenia gravis) graft v. host rejection, allograft rejections, fever and myalgia due to infection, AIDS related complex (ARC), keloid formation, scar tissue formation, Crohn's disease, ulcerative colitis and pyresis, irritable bowel syndrome, osteoporosis, cerebral malaria and bacterial meningitis, bowel pain, cancer pain, back pain, fibromyalgia, post-operative pain.

The amount of a compound of formula (I) that is administered to a subject is preferably an amount which gives rise to a peak plasma concentration that is less than the EC50 value of the compound at adenosine receptors at pH 7.4.

It will be appreciated that the EC50 value of the compound is likely to be different for different adenosine receptors (i.e. the A1, A2A, A2B, A3 adenosine receptors). The amount of the compound that is to be administered should be calculated relative to the lowest EC50 value of the compound at the different receptors.

Preferably the peak plasma concentration is one thousandth to one fifth, or one fiftieth to one third (more preferably one thousandth to one twentieth, one hundredth or one fiftieth to one fifth, one fiftieth to one tenth, or one tenth to one fifth) of the EC50 value. Preferably the amount administered gives rise to a plasma concentration that is maintained for more than one hour between one thousandth and one fifth, or one thousandth and one twentieth, or one hundredth and one fifth, or one fiftieth and one fifth, of the EC50 value of the compound at adenosine receptors at pH 7.4.

For the avoidance of doubt, the EC50 value of a compound is defined herein as the concentration of the compound that provokes a receptor response halfway between the baseline receptor response and the maximum receptor response (as determined, for example, using a dose-response curve).

The EC50 value should be determined under standard conditions (balanced salt solutions buffered to pH 7.4). For EC50 determinations using isolated membranes, cells and tissues this would be in buffered salt solution at pH 7.4 (e.g. cell culture medium), for example as in (Daly et al., Pharmacol. (1993) 46, 91-100), or preferably as in Tilburg et al (J. Med. Chem. (2002) 45, 91-100). The EC50 could also be determined in vivo by measuring adenosine receptor mediated responses in a normal healthy animal, or even in a tissue perfused under normal conditions (i.e. oxygenated blood, or oxygenated isotonic media, also buffered at pH 7.4) in a normal healthy animal.

Alternatively, the amount of a compound of formula (I) that is administered may be an amount that results in a peak plasma concentration that is one thousandth to one twentieth, one thousandth to one third, more preferably one hundredth to one fifth, or one fiftieth to one tenth, of the Kd value at adenosine receptors.

It will be appreciated that the Kd value of the compound is likely to be different for different adenosine receptors (i.e. the A1, A2A, A2B, A3 adenosine receptors). The amount of the compound that is to be administered should be calculated relative to the lowest Kd value of the compound for the different receptors.

Preferably the amount of the compound that is administered is an amount that results in a plasma concentration that is maintained for at least one hour between one thousandth and one fifth, more preferably between one thousandth and one twentieth, or one hundredth and one fifth, or one fiftieth and one fifth, of the Kd value of the compound at adenosine receptors.

The Kd value of the compound at each receptor should be determined under standard conditions using plasma membranes as a source of the adenosine receptors derived either from tissues or cells endogenously expressing these receptors or from cells transfected with DNA vectors encoding the adenosine receptor genes. Alternatively whole cell preparations using cells expressing adenosine receptors can be used. Labelled ligands (e.g. radiolabelled) selective for the different receptors should be used in buffered (pH 7.4) salt solutions (see e.g. Tilburg et al, J. Med. Chem. (2002) 45, 420-429) to determine the binding affinity and thus the Kd of the compound at each receptor.

Alternatively, the amount of a compound of formula (I) that is administered may be an amount that is one thousandth to one fifth, or one fiftieth to one third (preferably one thousandth to one twentieth, or one hundredth or one fiftieth to one fifth) of the minimum dose of the compound that gives rise to bradycardia, hypotension or tachycardia side effects in animals of the same species as the subject to which the compound is to be administered. Preferably the amount is one tenth to one fifth of the minimum dose that gives rise to the side effects. Preferably the amount administered gives rise to a plasma concentration that is maintained for more than 1 hour between one thousandth and one twentieth, or one hundredth or one fiftieth and one fifth of the minimum dose that gives rise to the side effects.

Alternatively, the amount of a compound of formula (I) that is administered may be an amount that gives rise to plasma concentrations that are one thousandth to one fifth, or one fiftieth to one third (preferably one thousandth to one twentieth, or one hundredth or one fiftieth to one fifth) of the minimum plasma concentration of the compound that cause bradycardia, hypotension or tachycardia side effects in animals of the same species as the subject to which the compound is to be administered. Preferably the amount gives rise to plasma concentrations that are one tenth to one fifth of the minimum plasma concentration that causes the side effects. Preferably the amount administered gives rise to a plasma concentration that is maintained for more than 1 hour between one thousandth and one twentieth, or one hundredth or one fiftieth and one fifth, of the minimum plasma concentration that causes the side effects.

It is expected that the amount of a compound of formula (I) that is administered should be 0.01 to 15 mg/kg, for example 0.01 to 5 or 10 mg/kg. Preferably the amount is less than 6 mg/kg, for example 0.01 to 2 mg/kg. Preferably the amount is at least 0.01 or 0.1 mg/kg, for example 0.1 to 2 mg/kg, or 0.2 to 1 mg/kg. A typical amount is 0.2 or 0.6 to 1.2 mg/kg.

Preferred doses for a 70 kg human subject are less than 420 mg, preferably at least 0.7 mg, more preferably at least 3.5 mg, most preferably at least 7 mg. More preferably 7 to 70 mg, or 14 to 70 mg.

The dosage amounts specified above are significantly lower (up to approximately 100 times lower) than would be expected (based on the EC50 value of spongosine at the adenosine A2A receptor) to be required for the compounds of formula (I) to have any beneficial therapeutic effect.

The appropriate dosage of a compound of formula (I) will vary with the age, sex, weight, and condition of the subject being treated, the potency of the compound, and the route of administration, etc. The appropriate dosage can readily be determined by one skilled in the art.

A compound of formula (I) may be administered with or without other therapeutic agents, for example analgesics or anti-inflammatories (such as opiates, steroids, NSAIDs, cannabinoids, tachykinin modulators, or bradykinin modulators) or anti-hyperalgesics (such as gabapentin, pregabalin, cannabinoids, sodium or calcium channel modulators, anti-epileptics or anti-depressants).

It has been found that additive analgesic effects can be obtained if spongosine is administered with another analgesic agent. Thus, spongosine and the other analgesic agent can be administered to obtain a desired level of analgesic effect, each at a lower dose than would be required to achieve that level if either agent was administered alone. Because lower doses of each agent can be administered, side effects associated with administration of higher doses of the agents are reduced. Alternatively, an increased level of analgesic effect can be obtained by administering spongosine and the other analgesic agent at higher doses. It is believed that this will also be the case with the other compounds of formula (I).

The preferred dosage of a compound of formula (I) when administered with another analgesic agent is lower than a preferred dosage specified above for administration of the compound alone.

It is believed that an additive analgesic effect is achieved if the other analgesic agent does not act in the same way as the compound of formula (I). Suitable other analgesic agents that may be administered with the compound include opioid receptor agonists and partial agonists (such as morphine, diamorphine, fentanyl, buprenorphine, codeine, or derivatives thereof), cyclooxygenase inhibitors (such as aspirin, paracetamol, ibuprofen, diclofenac, or derivatives thereof), sodium or calcium channel modulators (such as lignocaine, or gabapentin), or Selective Serotonin Reuptake Inhibitors (SSRI's) (such as paxil).

Example 5 below shows that the anti-hyperalgesic properties of spongosine are unaffected by co-administration of the opioid receptor antagonist naloxone indicating that spongosine does not act via an opioid receptor. Example 6 below demonstrates the additive analgesic effects of co-administration of spongosine and gabapentin. Gabapentin is effective against neuropathic pain. It is expected that other analgesic agents that are designed to treat neuropathic pain may have additive analgesic effects with compounds of formula (I). Such agents include topamax, pregabalin, ziconitide, and cannabinoid derivatives.

In general, a compound of formula (I) may be administered by known means, in any suitable formulation, by any suitable route. A compound of the invention is preferably administered orally, parenterally, sublingually, transdermally, intrathecally, or transmucosally. Other suitable routes include intravenous, intramuscular, subcutaneous, inhaled, and topical. The amount of drug administered will typically be higher when administered orally than when administered, say, intravenously.

It will be appreciated that a compound of formula (I) may be administered together with a physiologically acceptable carrier, excipient, or diluent.

Suitable compositions, for example for oral administration, include solid unit dose forms, and those containing liquid, e.g. for injection, such as tablets, capsules, vials and ampoules, in which the active agent is formulated, by known means, with a physiologically acceptable excipient, diluent or carrier. Suitable diluents and carriers are known, and include, for example, lactose and talc, together with appropriate binding agents etc.

A unit dosage of a compound of the invention typically comprises up to 500 mg (for example 1 to 500 mg, preferably 5 to 500 mg) of the active agent. Preferably the active agent is in the form of a pharmaceutical composition comprising the active agent and a physiologically acceptable carrier, excipient, or diluent. The preferred dosage is 0.1 to 2, e.g. 0.5 to 1, typically about 0.2 or 0.6, mg of the active agent per kg of the (human) subject. At these levels, effective treatment can be achieved substantially without a concomitant fall (for example, no more than 10%) in blood pressure.

Preferably a compound of formula (I) is administered at a frequency of 2 or 3 times per day.

Embodiments of the invention may exclude 2-propoxyadenosine, 2-isopropoxyadenosine, 3' deoxy 2 methoxyadenosine and 3' deoxy 2 ethoxyadenosine.

DESCRIPTION OF DRAWINGS

Embodiments of the invention are described in the following examples with reference to the accompanying drawings in which.

EXAMPLES

Example 1

Figure 1:
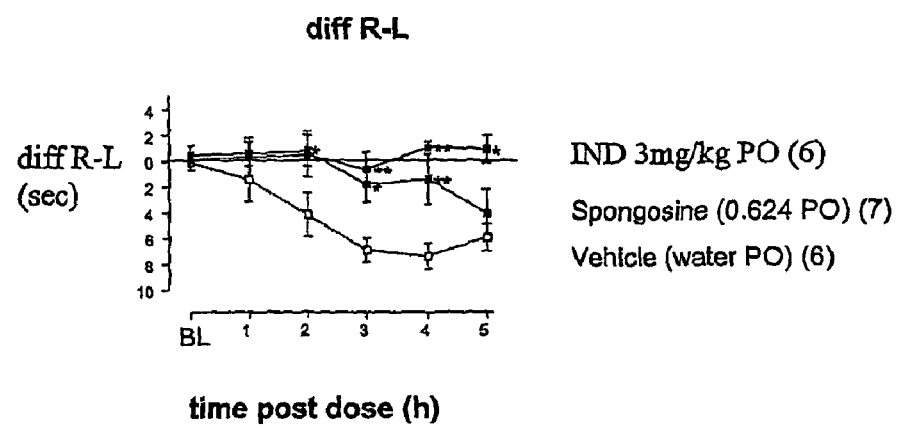
FIG. 1 shows the anti-hyperalgesic actions of spongosine (0.6 mg/kg p.o.) on carrageenan induced hyperalgesia. A: time course; B: dose dependency of the anti-hyperalgesic effect.
Figure 1:
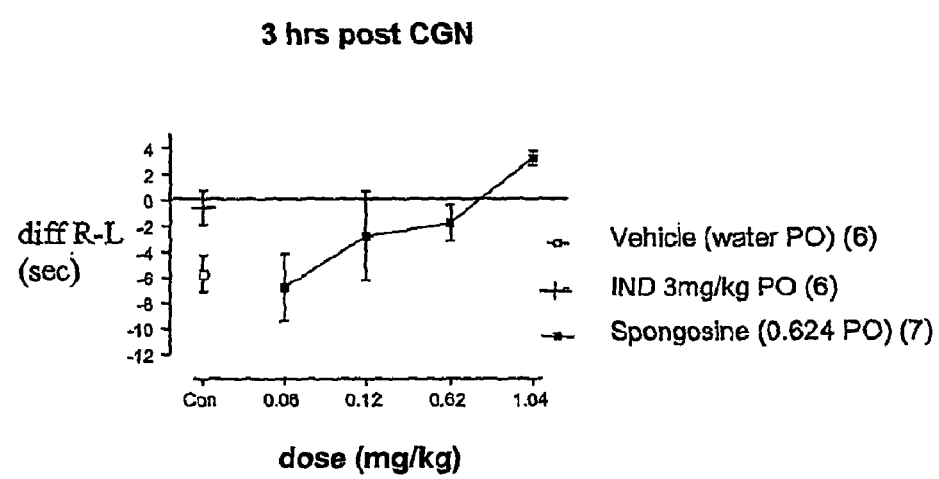

FIG. 1: A. Spongosine (0.624 mg/kg p.o.) inhibits carrageenan (CGN) induced thermal hyperalgesia (CITH) with comparable efficacy to indomethacin (3 mg/kg, po). B. Concentration-response relationship for Spongosine at 3 hrs post dosing. Carrageenan (2%, 10 microlitres) was administered into the right hind paw. A heat source was placed close to the treated and untreated hind paws, and the difference in the paw withdrawal latencies is shown. Spongosine was administered at the same time as carrageenan. Spongosine was as effective as indomethacin (Indo, 3 mg/kg p.o.).

Example 2

Figure 2:
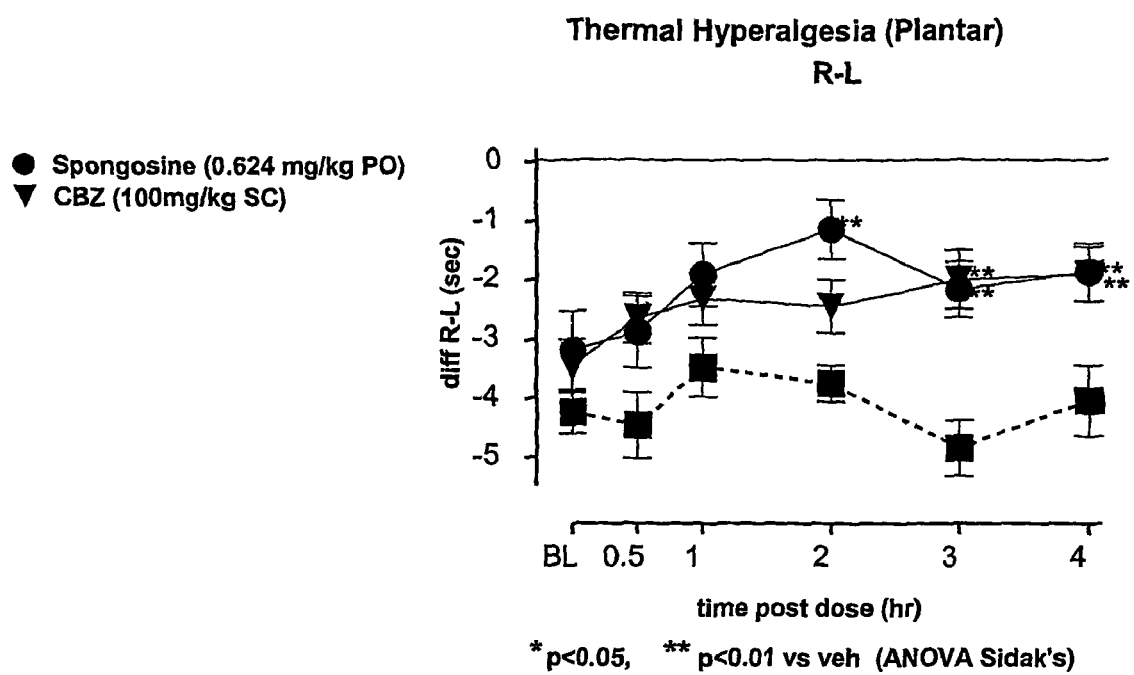
FIG. 2 shows the anti-hyperalgesic actions of spongosine (0.6 mg/kg p.o.) in the chronic constriction injury model of neuropathic pain.

FIG. 2: Spongosine (0.624 mg/kg p.o.) inhibits thermal hyperalgesia caused by chronic constriction injury of the rat sciatic nerve. Under anaesthesia the sciatic nerve was displayed in the right leg, and four loose ligatures tied round the nerve bundle. After approximately two weeks the rats developed thermal hyperalgesia in the operated leg as judged by the difference in paw withdrawal latencies of the right and left paws. Administration of spongosine reduced the hyperalgesia as shown by the reduction in the difference between the withdrawal latencies. Spongosine was as, or more, effective than carbamazepine (CBZ, 100 mg/kg s.c.)

Example 3

Figure 3:
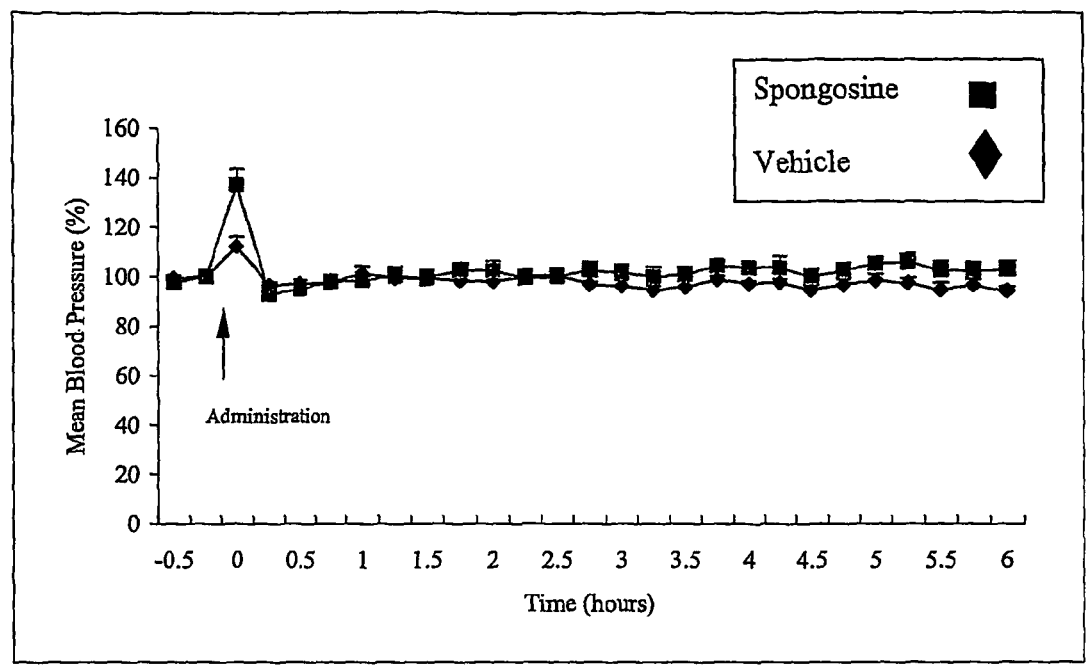
FIG. 3 shows the effect of spongosine (0.6 mg/kg p.o.) on A: blood pressure in normal rats; B: heart rate.
Figure 3:
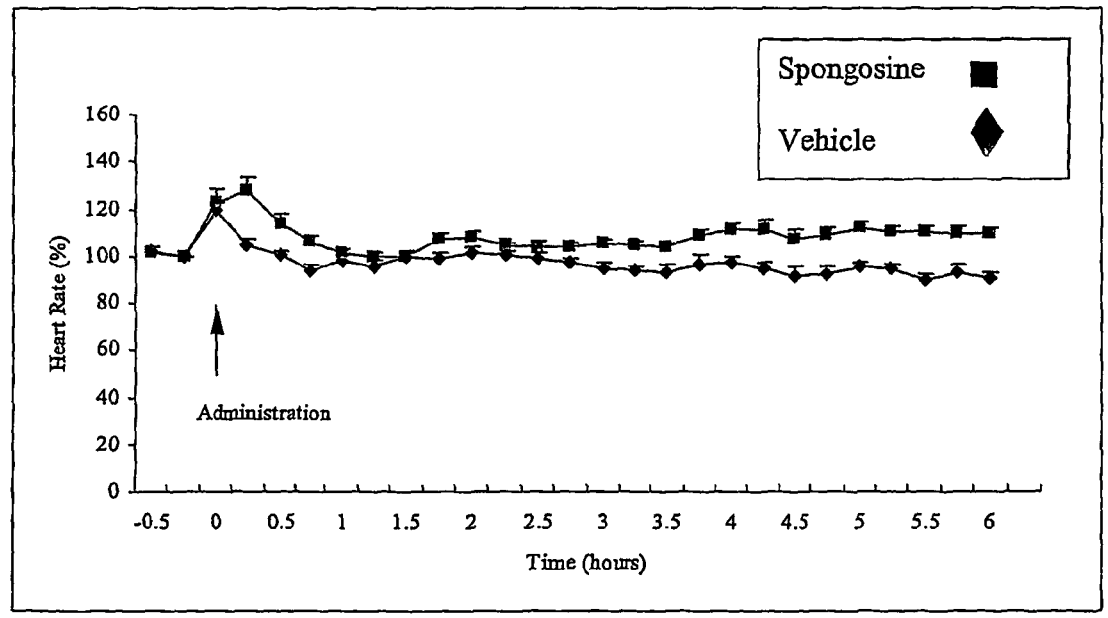

FIG. 3: Spongosine (0.624 mg/kg p.o.) has no significant effect on blood pressure or heart rate. An implantable radio-telemetry device was placed in the abdominal cavity of 6 rats per group. The pressure catheter of the device was inserted in the abdominal aorta and two electrodes tunnelised under the skin in a lead II position (left side of abdominal cavity/right shoulder). Individual rats were placed in their own cage on a radioreceptor (DSI) for data acquisition. A: blood pressure; B: heart rate.

Example 4

Figure 4:
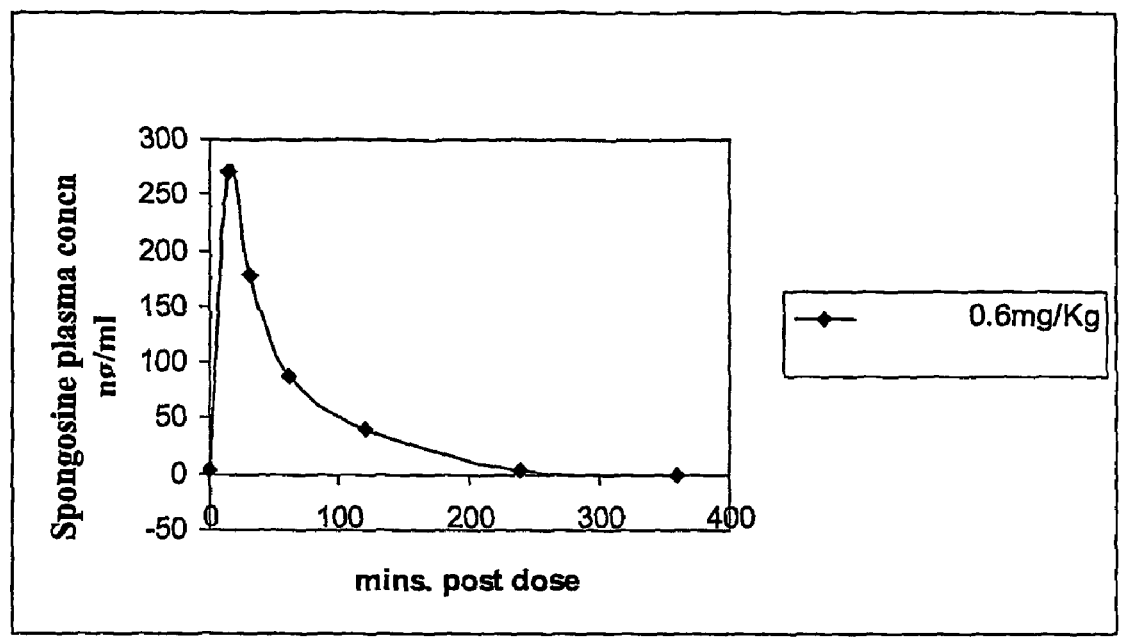
FIG. 4 shows the change in plasma concentration over time after administration of spongosine.

The EC50 value of spongosine at adenosine receptors (measured at pH 7.4) is 900 ng/ml (3 µM). FIG. 4 shows the change in plasma concentration over time after administration of spongosine at 0.6 mg/kg to a rat. It can be seen that the plasma concentration remains above 2% of the EC50 value for more than 3 hours. Anti-hyperalgesic effects have been observed (without blood pressure changes) when the peak plasma concentration is between 1% and 30% of the EC50 value determined in vitro. If the peak plasma concentration reaches the EC50 value profound reductions in blood pressure occur that last for hours.

Example 5

Figure 5:
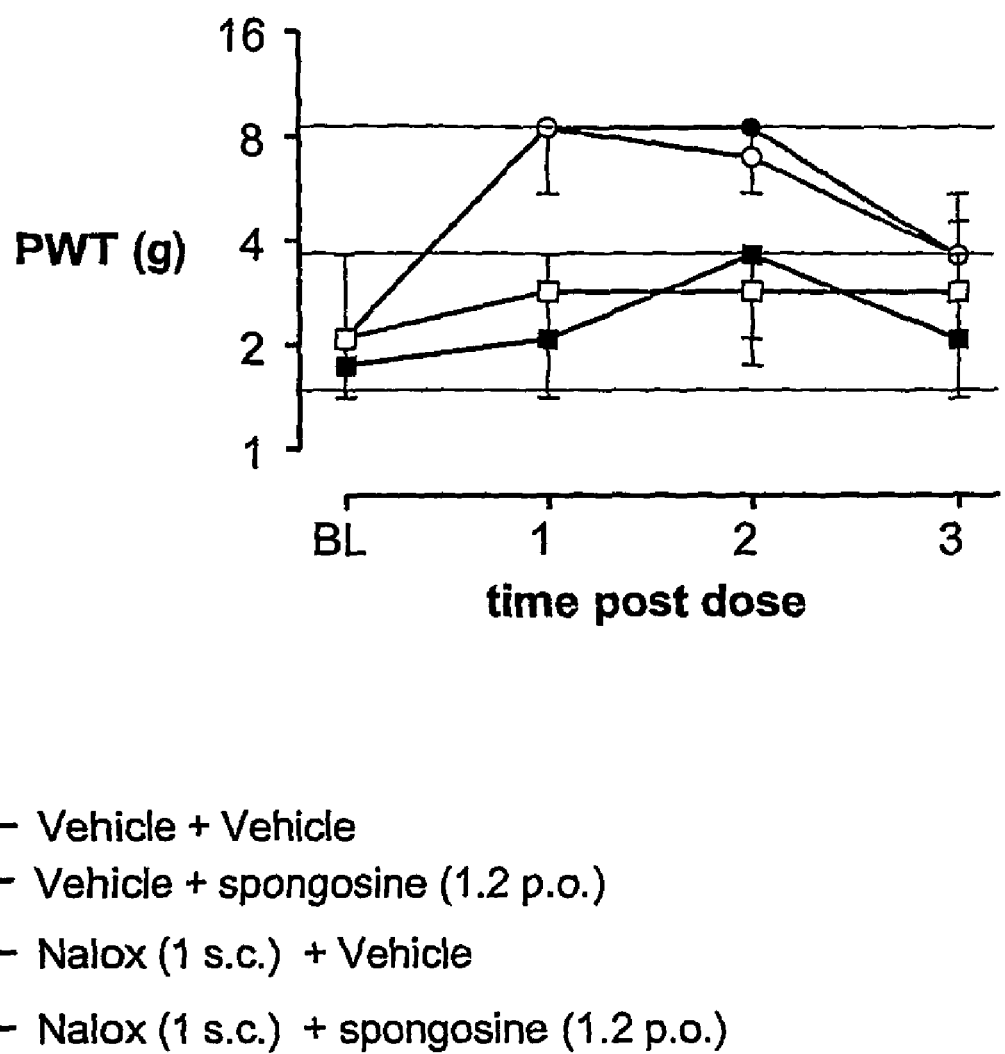
FIG. 5 shows the effect of spongosine (0.6 mg/kg p.o.) in the presence and absence of naloxone in a model of neuropathic pain.

FIG. 5: Spongosine (1.2 mg/kg p.o.) inhibits static allodynia in a model of neuropathic pain, both in the presence and absence of naloxone (1 mg/kg s.c.). Administration of spongosine reduced the hyperalgesia as shown by the increased paw withdrawal threshold (PWT) in the presence and absence of naloxone. Veh: vehicle.

Example 6

Figure 6:
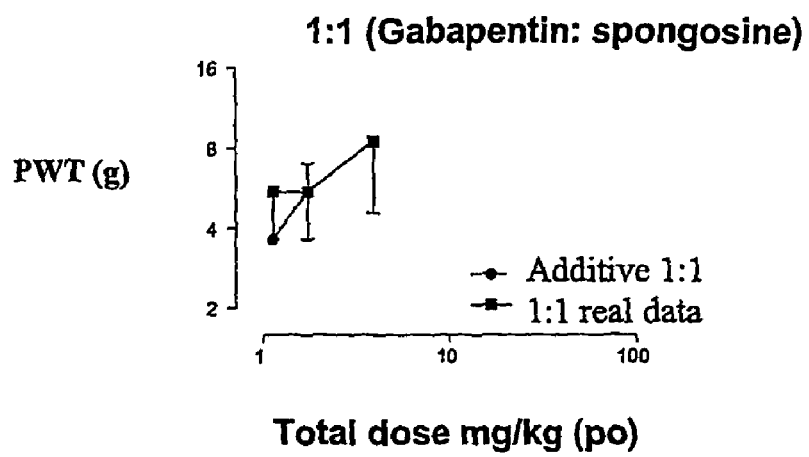
FIG. 6 shows the additive effect of spongosine and gabapentin in a model of neuropathic pain.
Figure 6:
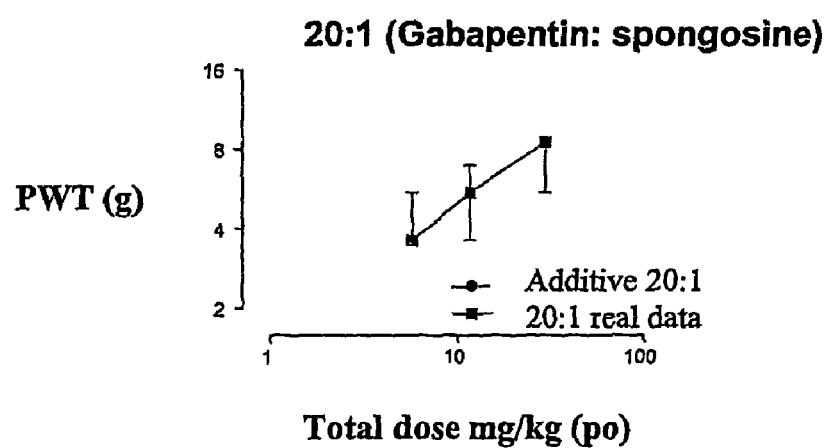
Figure 6:
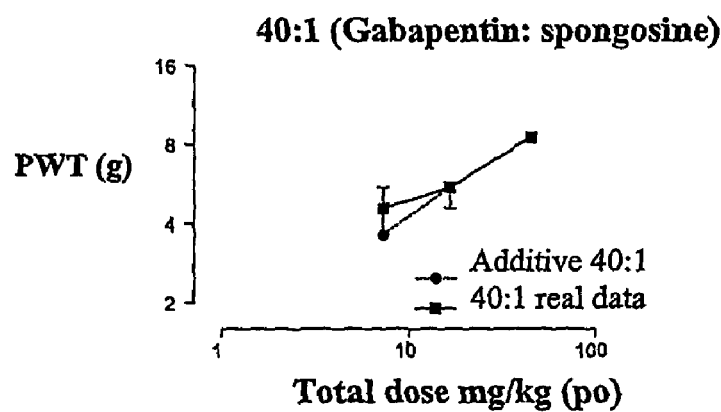

FIG. 6: Spongosine and gabapentin inhibit static allodynia in a model of neuropathic pain. Spongosine and gabapentin were administered (p.o.) in different proportions as indicated in the drawing. The total dose administered is shown on the horizontal axis, and the paw withdrawal threshold (PWT) on the vertical axis. The predicted anti-hyperalgesic effect (derived from the dose response curves obtained with each agent alone) if the effects of the two compounds are additive is shown (●). The observed effects are indicated by (■). It is apparent that the observed effects are not significantly different from those predicted by additivity.

Spongosine is effective in inhibiting pain perception in mammals suffering from neuropathic and inflammatory pain even when administered at doses expected to give concentrations well below those known to activate adenosine receptors. At these doses it can be seen that neither the heart A1 receptors nor the vascular A2A receptors are sufficiently stimulated to cause a change in the cardiovascular status of the animals.

Compounds of formula (I) can be used as analgesics particularly anti-hyperalgesics) which can be administered orally for the treatment of pain (particularly hyperalgesia) caused as a result of neuropathy and/or inflammatory disease, including Diabetic Neuropathy, polyneuropathy, Cancer Pain, Fibromyalgia, Myofascial Pain Syndrome, Pancreatic Pain, Pelvic/Perineal pain, back pain, Post Herpetic Neuralgia, Rhematoid Arthritis, Sciatica/Lumbar Radiculopathy, Spinal Stenosis, Temporo-mandibular Joint Disorder, HIV pain, Trigeminal Neuralgia, Chronic Neuropathic Pain, Lower Back/pain, Failed Back Surgery pain, post operative pain, post physical trauma pain (including gunshot, RTA, burns), Cardiac pain, Chest pain, Pelvic pain/PID, Joint pain (tendonitis, bursitis, acute arthritis), Neck Pain, Bowel pain, Phantom limb pain, Obstetric Pain (labour/C-Section), Renal Colic, Acute Herpes Zoster Pain, Acute Pancreatitis Breakthrough Pain, Cancer pain, Dysmenorhoea/Endometriosis, rheumatoid arthritis, osteoarthritis, rheumatoid spondylitis, gouty arthritis, and other arthritic conditions, cancer, HIV, chronic pulmonary inflammatory disease, silicosis, pulmonary sarcosis, bone resorption diseases, reperfusion injury (including damage caused to organs as a consequence of reperfusion following ischaemic episodes e.g. myocardial infarcts, strokes), autoimmune damage (including multiple sclerosis, Guillam Baxre Syndrome, myasthenia gravis) graft v. host rejection, allograft rejections, fever and myalgia due to infection, AIDS related complex (ARC), keloid formation, scar tissue formation, Crohn's disease, ulcerative colitis and pyresis, irritable bowel syndrome, osteoporosis, cerebral malaria and bacterial meningitis.

The invention claimed is:

1. A method of treating pain which comprises administering a side-effect-avoiding dosage of a compound of formula (I) to a human subject in need of such treatment:

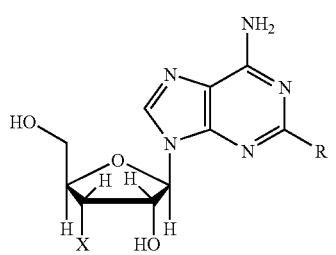

wherein R is $C_{1-4}$ alkoxy, and X is H, excluding 2-methoxy-adenosine.

2. The method of claim 1, wherein the pain is hyperalgesia.

3. The method of claim 2, wherein the hyperalgesia is neuropathic pain.

4. The method of claim 1, wherein the pain is caused by or associated with damaged sensory neurons.

5. The method of claim 2, wherein the hyperalgesia is inflammatory pain.

6. The method of claim 1, wherein the pain is caused by or associated with inflammation or tissue damage.

7. The method of claim 1, wherein the compound is administered at a dose that gives rise to a peak plasma concentration of the compound that is less than the EC50 value of the compound at adenosine receptors at pH 7.4.

8. The method of claim 1, wherein the compound is administered at a dose that is one thousandth to one fifth of the minimum dose of the compound that gives rise to bradycardia, hypotension or tachycardia side effects in animals of the same species as the subject to which the dose is to be administered.

9. The method of claim 8, wherein the dose is one hundredth to one fifth of the minimum dose that gives rise to the side effects.

10. The method of claim 1, wherein the compound is administered at a dose that results in a plasma concentration of the compound that is maintained for more than one hour between one hundredth and one fifth of the minimum dose of the compound that gives rise to bradycardia, hypotension or tachycardia side effects in animals of the same species as the subject to which the compound is to be administered.

11. The method of claim 1, wherein the compound is administered at a dose of less than 6 mg/kg.

12. The method of claim 1, wherein the compound is administered at a dose of at least 0.01 mg/kg.

13. The method of claim 1, wherein the compound is administered at a dose of 0.2 to 1 mg/kg.

14. The method of claim 1, wherein the compound is administered orally, parenterally, sublingually, transdermally, intrathecally, transmucosally, intravenously, intramuscularly, subcutaneously, topically, or by inhaling.

15. The method of claim 1, wherein the compound is administered at a frequency of 2 or 3 times per day.

16. The method of claim 1, wherein the subject is a human subject.

* * * * *

UNITED STATES PATENT AND TRADEMARK OFFICE
CERTIFICATE OF CORRECTION

PATENT NO.        : 7,759,321 B2                                        Page 1 of 1
APPLICATION NO.   : 10/547455
DATED             : July 20, 2010
INVENTOR(S)       : Peter Richardson, Kevin Lee and Lisa Lione It is certified that error appears in the above-identified patent and that said Letters Patent is hereby corrected as shown below:

Title Page; item (57); On the First Page, Col. 2 (Abstract), Line 8, delete

"
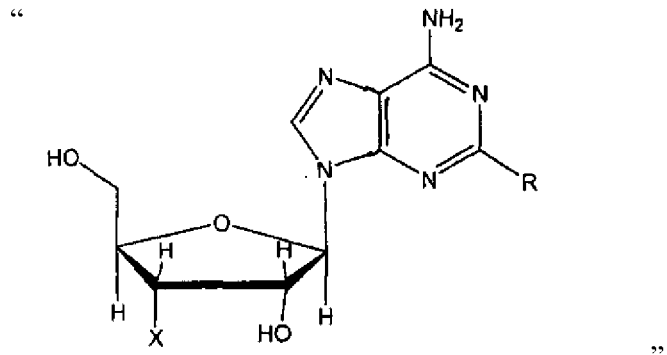
"

and insert

--
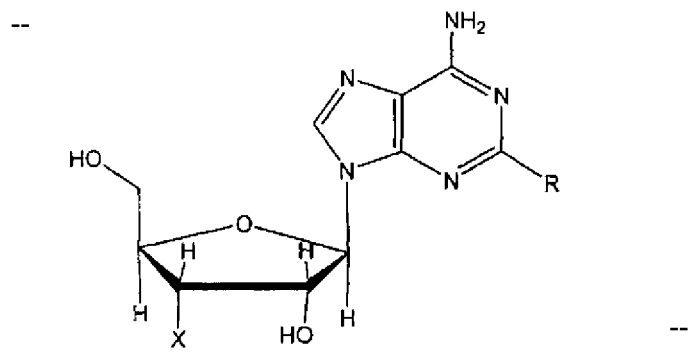
--

Signed and Sealed this

Twenty-eighth Day of September, 2010

David J. Kappos
*Director of the United States Patent and Trademark Office*